US012721872B1

(12) United States Patent
Cornell et al.

(10) Patent No.: US 12,721,872 B1
(45) Date of Patent: Sep. 1, 2026

(54) COMPOSITIONS AND METHODS FOR TREATING DAMAGED SKIN

(71) Applicant: CODEX LABS CORPORATION, San Jose, CA (US)

(72) Inventors: Marc Cornell, San Jose, CA (US); Barbara A. Paldus, San Jose, CA (US)

(73) Assignee: CODEX LABS CORPORATION, San Jose, CA (US)

( * ) Notice: Subject to any disclaimer, the term of this patent is extended or adjusted under 35 U.S.C. 154(b) by 0 days.

(21) Appl. No.: 19/351,956

(22) Filed: Oct. 7, 2025

(51) Int. Cl.

| | |
|---|---|
| ***A61K 36/03*** | (2006.01) |
| ***A61K 36/28*** | (2006.01) |
| ***A61K 36/539*** | (2006.01) |
| ***A61K 36/81*** | (2006.01) |
| ***A61K 36/889*** | (2006.01) |
| ***A61P 17/02*** | (2006.01) |
| ***A61P 17/18*** | (2006.01) |

(52) U.S. Cl.
CPC .............. *A61K 36/03* (2013.01); *A61K 36/28* (2013.01); *A61K 36/539* (2013.01); *A61K 36/81* (2013.01); *A61K 36/889* (2013.01); *A61P 17/02* (2018.01); *A61P 17/18* (2018.01)

(58) Field of Classification Search
None
See application file for complete search history.

(56) References Cited

U.S. PATENT DOCUMENTS 8,101,211 B2 * 1/2012 Chiba .................... A61P 29/00
424/401
2020/0405589 A1 * 12/2020 Omura .................... A61K 8/42

FOREIGN PATENT DOCUMENTS

WO WO-2010002586 A2 * 1/2010 .............. A61P 17/00

* cited by examiner

*Primary Examiner* — Susan Hoffman
(74) *Attorney, Agent, or Firm* — MEDLER FERRO WOODHOUSE & MILLS PLLC

(57) ABSTRACT

The present invention relates to a composition for treating damaged skin, the composition comprising a synergistic mixture of: (a) from about 0.1 to about 5% by weight of *Padina pavonica* extract; (b) from about 0.1 to about 5% by weight of *Scutellaria baicalensis* extract; (c) from about 0.1 to about 5% by weight of *Physalis angulata* extract; and (d) from about 1 to about 5% by weight of an emulsifier, all weights based on the total weight of the composition.

24 Claims, 2 Drawing Sheets
(2 of 2 Drawing Sheet(s) Filed in Color)

COMPOSITIONS AND METHODS FOR TREATING DAMAGED SKIN

FIELD OF THE INVENTION

The present invention is directed to compositions and methods for treating damaged skin. More particularly, the present invention relates to a novel and synergistic combination of plant-based extracts which, when combined, help to promote healing in damaged skin.

BACKGROUND

Damaged or injured skin is biologically characterized by impaired skin barrier function, altered cellular processes, and a compromised extracellular matrix. As skin ages, endures chronic environmental insult and/or is subject to chronic inflammatory skin disorders, it experiences: (i) impaired skin barrier function; (ii) altered cellular processes; (iii) a compromised extracellular matrix; and (iv) inflammatory responses.

Regarding impaired skin barrier function, a damaged/injured skin barrier cannot effectively retain moisture which leads to skin dehydration and increased water loss via the epidermis. In addition, the protective lipid structures in the outermost layer of skin (stratum corneum) can become dysfunctional or decreased, resulting in a reduction in skin's ability to prevent water loss and block irritants. The tight junctions that bind skin cells together can also become compromised, causing skin cells to swell and the intercellular spaces within the skin barrier to widen. This, in turn, weakens the skin barrier and allows for increased penetration of allergens and unwanted microorganisms. Also, the damaged/injured skin barrier's inability to prevent the entry of problematic external agents renders the body more vulnerable to infections and dermatological diseases.

When it comes to altered cellular processes, damaged cells may undergo senescence, a permanent halt in cell division, to prevent proliferation of damaged cells. The problem is that senescent cells accumulate with age and release inflammatory cytokines, growth factors, and proteases. The ability of skin cells to regenerate is also impaired when skin is damaged and, in aging skin, wound healing can also be significantly slower. In addition, an imbalance between the production of reactive oxygen species (ROS) such as free radicals, and the body's ability to neutralize them can cause cellular damage. This leads to the degradation of lipids, proteins, and DNA within skin cells. Moreover, damaged skin can also disrupt the natural balance of microorganisms on the skin. A shift in the microbial community can affect the skin barrier's integrity and contribute to conditions like acne.

When skin is damaged/injured, it also experiences changes in its extracellular matrix. Damaged skin shows a decrease in the production, and increase in the breakdown, of collagen and elastin, the proteins responsible for skin's firmness and elasticity. UV radiation and oxidative stress can cause breaks in DNA strands which, if left unrepaired, can lead to cellular dysfunction and photoaging.

Further, inflammation in damaged skin is characterized by the release of pro-inflammatory cytokines which serve to further disrupt the structure and functionality of the skin barrier. Regarding chronic inflammation such as the kind involved in certain skin disorders (rosacea, eczema, acne, etc.) or resulting from the skin aging process, chronic inflammation promotes tissue damage and impairs repair mechanisms by stimulating MMPs and collagen breakdown. Moreover, damaged/injured skin triggers an immune response by the body, attracting innate immune cells like keratinocytes and Langerhans cells to the injury site.

In short, when skin is damaged/injured, it experiences a general reduction in cellular and tissue vitality, reduction in cell replications rates, reduced cutaneous blood flow, reduced moisture content, accumulated errors in skin barrier structure and function, alterations in the normal regulation of common biochemical pathways, and a reduction in the skin's ability to remodel and repair itself. A tell-tale "visible" sign that skin has been damaged/injured, regardless of the cause, is "erythema."

Erythema is a skin condition characterized by abnormal redness of the skin. It is a medical condition that is more severe than normal flushed skin experienced by those with sensitive or fair skin. It can occur in response to a variety of skin-related conditions such as, for example, flare-ups from chronic skin disorders like eczema, psoriasis, or rosacea; prolonged exposure to the sun (sunburn); phototherapy for acne, eczema or psoriasis treatment; and skin remodeling laser treatments and micro-needling for aesthetic reasons.

Extrinsic factors that can damage the skin are oftentimes difficult or impossible to avoid. When skin is damaged the keratinocyte (outermost cell of the skin) releases signaling molecules, such as inflammatory cytokines. Their release, though helpful in terms of initiating the skin recovery process, can also trigger undesired outcomes such as erythema, inflammation, increased temperature of the skin, and eventually, skin damage.

Examples of extrinsic skin-damaging factors include excessive exposure to the sun's UV rays, chronic exposure to environmental pollutants, phototherapy treatments for skin conditions such as acne, eczema or psoriasis, aesthetic skin remodeling procedures involving the use of lasers, irritation caused by contact with skin-irritating substrates such as certain plants (poison ivy/oak), harsh chemicals, and the like.

Exposure to UV radiation is known to cause direct DNA damage within skin cells and can additionally lead to forms of indirect DNA damage through ROS generation. In addition to causing DNA damage, ROS generated by UV exposure can damage other components of the cell (e.g., proteins, lipids, and organelles). Sufficient DNA damage or even an excess in the cellular levels of ROS can initiate apoptosis, a form of programmed cell death, and/or an inflammatory response. ROS and other free radicals are generated during inflammation and can further impact the health and homeostasis of the skin. For example, during this cascade of events, enzymes are activated in the skin to break down collagen. Taken together, the direct DNA damage and ROS generation caused by UV exposure contribute to skin experiencing erythema and skin barrier damage.

In addition, collagen fibers in the skin are reduced by exposure to ultraviolet radiation, a dry environment, and oxidation by reactive oxygen species (ROS) such as free radicals. Reduction of collagen is associated with reduced skin resilience and elasticity. Increased collagen production improves skin healing in patients with erythema. Moreover, maintenance and/or increases in collagen levels in the skin help to maintain skin function and appearance.

Cosmetic procedures that expose skin to mechanical stress such as chemical peels, micro-needling and facial laser treatment cause the skin barrier to become immediately compromised, i.e., damaged/injured. The typical impact such procedures have on the skin barrier includes: disruption of the barrier's lipid matrix caused by ceramides, fatty acids, and cholesterol being stripped therefrom; an increase in TEWL (Trans Epidermal Water Loss) due to the barrier's inability to retain moisture; inflammation & redness, i.e., erythema which represents an inflammatory response by the body to activate its healing process which, in turn, causes irritation and prolongs the skin's recovery time; heightened sensitivity to irritants, allergens, and environmental aggressors; and compromised protection and increased risk of Infection which enables easier access for bacteria, viruses & pathogens to enter the body.

Recent studies have revealed that cosmetic facial laser treatments continue to affect skin's structure and appearance long after the healing period ends. Unlike immediate side effects such as redness or swelling, these delayed manifestations emerge gradually, often becoming noticeable 18-36 months post-treatment. These manifestations include pigmentary changes, scarring, persistent redness (erythema); changes in skin texture; and milia formation.

Post-Inflammatory Hyperpigmentation (PIH) is a common phenomenon experienced by those individuals with darker skin tones (Fitzpatrick III-VI). Hypopigmentation occurs when deeper laser treatments or peels damage melanocytes within the skin.

When it comes to scarring, there are three common types. Hypertrophic scarring is characterized by elevated, thickened scars within original treatment area. Keloid scarring is a more aggressive form characterized by raised scars beyond the original treatment area. Atrophic scarring takes the form of depressed or pitted scars.

Additional side-effects of cosmetic procedures include changes in skin texture and uniformity, i.e., skin roughness; persistent redness (i.e., erythema) especially for individuals with inherently sensitive skin caused by damage to blood vessels or chronic inflammation; changes in skin texture including skin thinning, loss of elasticity; and the formation of milia which are generally benign and can be easily removed by a dermatologist.

Once skin has been damaged, regardless of the cause, a short, well-timed inflammatory phase triggers tissue remodeling. Neutrophils and macrophages act like a cleanup crew, releasing ROS and proteases to sterilize and digest damaged tissue, after which fibroblasts and keratinocytes begin to rebuild the skin matrix. Matrix metalloproteinases (MMP) temporarily soften the scaffolding so that new collagen and elastin can be laid. After which tissue inhibitors of MMPs, i.e., TIMPs, help reset balance.

Should the degree/extent of inflammation overshoot or persist, (i) excessive skin barrier matrix breakdown, (ii) delayed re-epithelialization, and (iii) either impaired healing due to a fragile/compromised skin barrier or excess repair, i.e., fibrosis/scarring of the injured area, are realized. Conversely, if this biological situation resolves in time, helped by pro-resolving mediators like lipoxins/resolvins, collagen is better aligned, vessels normalize, and erythema fades.

In short, when skin is damaged, a cascade of various biological processes is put into motion within the body. Erythema associated with inflammation and oxidative stress in the skin manifests as skin redness, representing a "visible" sign of skin damage/irritation. The skin barrier then begins to break down due to a lack of sufficient hydration, the inability to retain moisture caused by degradation of the skin barrier's lipid matrix, and the body's natural (biological) antioxidant system's failure to effectively neutralize free radicals and other ROS. Once the skin experiences erythema, inflammation, and a breakdown of its barrier function, the skin healing process is activated to help facilitate skin barrier repair and lipid matrix reinforcement.

Traditional treatments for helping skin recover after sustaining damage from, for example, skin micro-needling, skin laser resurfacing, chemical peels, and spending too much time in the sun, i.e., sunburn, tend to focus primarily on pain relief from the erythema their situation has caused. These traditional treatments include: gentle cleansing with mild, fragrance-free cleansers; topical application of skin hydrating products such as those containing humectants that draw moisture to the skin surface and emollients that help seal in the moisture; use of anti-inflammatory ingredients that help calm redness and irritation (erythema); and use of broad-spectrum sun protection to prevent further UV damage.

While these treatment options can certainly bring some level of relief to damaged skin to help promote the skin recovery process, a significant improvement in the outcomes they provide is still needed. There is, therefore, currently a significant need for a solution that can more effectively reduce erythema in the skin, post injury, while helping to optimize the body's skin/wound healing biological processes.

Based on the foregoing, it is an object of the present disclosure to provide skincare compositions and methods that are effective at treating erythema caused by external and/or internal factors. This is accomplished by mitigating inflammation and oxidative stress experienced by the skin, helping to repair and reinforce the skin barrier which has been compromised by inflammation and oxidative stress, and helping to accelerate the skin healing process.

SUMMARY OF THE INVENTION

In some embodiments, the present disclosure provides a composition for treating damaged skin comprising: (a) from about 0.1 to about 5% by weight of *Padina pavonica* extract; (b) from about 0.1 to about 5% by weight of *Scutellaria baicalensis* extract; (c) from about 0.1 to about 5% by weight of *Physalis angulata* extract; and (d) from about 1 to about 5% by weight of an emulsifier, all weights based on the total weight of the composition.

In further embodiments, the present disclosure provides a composition for treating erythema and promoting skin healing, the composition comprising: (a) from about 0.5 to about 3% by weight of *Padina pavonica* extract; (b) from about 0.5 to about 3% by weight of *Scutellaria baicalensis* extract; (c) from about 0.5 to about 3% by weight of *Physalis angulata* extract; and (d) from about 1.5 to about 4% by weight of an emulsifier, all weights based on the total weight of the composition.

In further embodiments, the present disclosure provides a composition for treating erythema and promoting skin healing, the composition comprising: (a) from about 1 to about 2% by weight of *Padina pavonica* extract; (b) from 1 to about 2% by weight of *Scutellaria baicalensis* extract; (c) from about 1 to about 2.5% by weight of *Physalis angulata* extract; and (d) from about 2 to about 3% by weight of an emulsifier, all weights based on the total weight of the composition.

The present disclosure also provides a method for treating damaged skin by topically applying one of the above-disclosed compositions onto damaged skin.

These and other features, aspects and advantages of the present disclosure will become evident to those skilled in the art from reading the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate exemplary embodiments of certain aspects of the present disclosure.

DETAILED DESCRIPTION OF THE INVENTION

Figure 1:
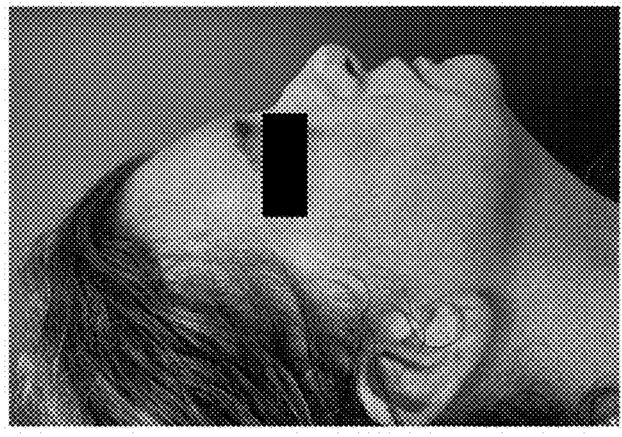
FIG. 1 is a series of side profile view photographs of a test subject's face following a skin micro-needling procedure (first photo), immediately after the micro-needling procedure (second photo) and post application of the composition of the present disclosure (third and fourth photos) evidencing the ability of the composition of the present disclosure to effectively treat skin that has been damaged by mechanical stress, due to the synergistic skin healing properties exhibited by the composition of the present disclosure.
Figure 1:
Figure 1:
Figure 1:
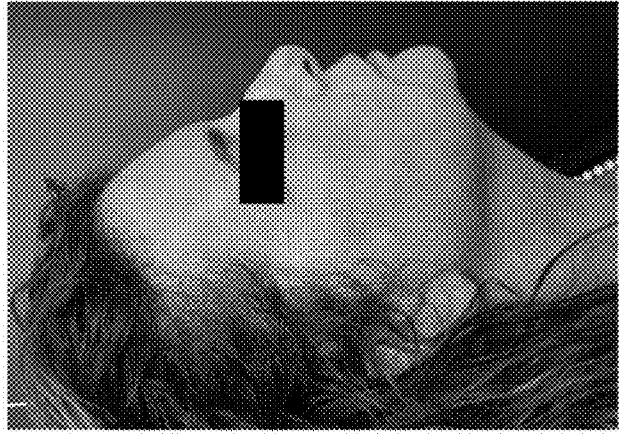

The compositions of the present invention can comprise, consist essentially of, or consist of, the components of the present disclosure as well as other ingredients described herein. The terms "comprising," "having," "including," and "containing," and variants thereof as used herein are inclusive or open-ended and do not exclude various optional, compatible components that can be used in the compositions of the present disclosure or additional steps that can be used in the methods of the present disclosure. The term "consisting essentially of" as used herein means that the composition or component may include additional ingredients, but only if the additional ingredients do not materially alter the basic and novel characteristics of the compositions or methods.

As used herein, the words "preferred," "preferably," and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice-versa, unless otherwise specified or clearly implied to the contrary by the context in which the reference is made.

As used herein, "about" can mean plus or minus 10% of the provided value. Where ranges are provided, they are inclusive of the boundary values. "About" can additionally or alternately mean either within 10% of the stated value, or within 5% of the stated value, or in some cases within 2.5% of the stated value; or, "about" can mean rounded to the nearest significant digit.

The term "or" as used herein means "and/or," unless explicitly indicated to refer only to alternatives or the alternatives are mutually exclusive, although the disclosure supports a definition that refers to only alternatives and "and/or."

All publications, articles, papers, patents, patent application publications, and other references cited herein are hereby incorporated in their entireties for all purposes to the extent consistent with the disclosure herein.

The term "oxidative stress" as described herein refers to the disturbance in balance between reactive oxygen species (ROS) and/or free radicals and antioxidants present in the skin caused by extrinsic and/or intrinsic factors. Extrinsic factors include, for example, exposure to UV radiation, high energy visible light, pollution, and products containing harsh chemicals. Intrinsic factors include, for example, chronological aging, a person's genetic makeup, and other biological changes that occur from within the skin.

The term "free radicals" as described herein refers to those ROS that are formed when skin experiences oxidative stress caused by extrinsic factors including exposure to UV radiation and environmental stressors such as pollution and harmful chemical agents typically found, for example, in hard-surface cleaning products.

The term "mechanical stress" as used herein refers to damage caused by the use of a mechanical/electromechanical device on the skin. Exemplary causes of mechanical stress include micro-needling and laser treatment, e.g., intense pulsed light (IPL) treatment and CO2 fractional laser treatment.

The present disclosure generally relates to compositions and methods for both treating erythema and promoting skin healing.

The inventors have surprisingly and unexpectedly discovered that the combination of specific plant-based extracts, namely, *Padina pavonica, Scutellaria baicalensis, Physalis Angulata*, and, optionally, a yarrow extract, yields a composition capable of synergistic gene modulation to help promote effective and efficient skin healing in damaged skin. It does so by positively influencing erythema, inflammation, oxidative stress, redox (antioxidant) control, skin barrier lipid matrix restoration, and skin healing/tissue remodeling.

*Padina pavonica*, a brown marine alga commonly found in Mediterranean coastal waters, contains a mix of bioactive compounds, including polysaccharides, polyphenols, fatty acids and minerals, that may contribute to skin repair and soothing properties. Studies have shown its extracts exhibit antioxidant and anti-inflammatory activities, which can reduce oxidative stress and inflammatory markers in damaged skin, supporting faster healing and reduced irritation. Polysaccharides from *P. pavonica* may also help maintain hydration and reinforce the skin barrier by forming a protective, film-forming layer that prevents transepidermal water loss. Additionally, certain fatty acids and minerals in the alga may promote re-epithelialization and may enhance collagen synthesis, which may aid tissue regeneration and improving skin elasticity and resilience after irritation or mild barrier compromise.

An example of a *Padina pavonica* extract in accordance with the present invention is commercially available from Gelyma, a French company headquartered in Marseille, under the tradename OCEA HEALTH®.

In some embodiments, the *Padina pavonica* extract is employed in the composition of the present disclosure in an amount of from about 0.1 to 5%, or from about 0.5 to about 3%, or from about 1 to about 2%, or about 2% by weight, all weights based on the total weight of the composition.

*Scutellaria baicalensis*, commonly known as Chinese skullcap, has been shown to have skin healing properties, attributed to its rich content of bioactive flavonoids, primarily baicalin, baicalein, and wogonin. These compounds exhibit significant anti-inflammatory, antioxidant, and antimicrobial activities. Studies have shown that baicalin and baicalein can effectively reduce oxidative stress and inhibit inflammatory cytokines in skin cells, promoting tissue repair and alleviating conditions like eczema and dermatitis. Additionally, the antimicrobial properties help prevent infections in compromised skin. The flavonoids also contribute to collagen production, enhancing skin elasticity and accelerating wound healing.

An example of a *Scutellaria baicalensis* extract in accordance with the present invention is commercially available from Exsymol, a Monaco-based company, under the tradename SCUTALINE®.

In some embodiments, the *Scutellaria baicalensis* extract is employed in the composition of the present disclosure in an amount of from about 0.1 to 5%, or from about 0.5 to about 3%, or from about 1 to about 2%, or about 2% by weight, all weights based on the total weight of the composition.

*Physalis angulata*, commonly known as the cutleaf groundcherry, is a plant recognized for its medicinal properties, including its potential benefits for skin healing. Rich in bioactive compounds such as flavonoids, withanolides, and alkaloids, *P. angulata* exhibits anti-inflammatory, antioxidant, and antimicrobial activities that may support skin regeneration. Studies have demonstrated that extracts from *P. angulata* can reduce oxidative stress and inflammation, which are key factors in delayed wound healing and skin irritation. Additionally, its antimicrobial properties help prevent infection in wounds, facilitating faster recovery. The plant's compounds may also promote collagen synthesis and tissue regeneration, helping to restore skin integrity and elasticity.

An example of a *Physalis angulata* extract in accordance with the present invention is commercially available from Chemyunion, under the tradename PHYSAVIE®.

In some embodiments, the *Physalis angulata* extract is employed in the composition of the present disclosure in an amount of from about 0.1 to 5%, or from about 0.5 to about 3%, or from about 1 to about 2.5%, or about 2.5% by weight, all weights based on the total weight of the composition.

*Achillea millefolium*, commonly known as yarrow, has been traditionally used for wound healing and skin repair due to its anti-inflammatory, antimicrobial, and hemostatic properties. The plant contains bioactive compounds such as flavonoids, sesquiterpens, and alkaloids, which contribute to reducing inflammation and promoting tissue regeneration. Studies have demonstrated that extracts of *A. millefolium* can accelerate wound healing by enhancing collagen synthesis and re-epithelialization, thereby contributing to faster skin repair. Additionally, its antimicrobial activity may help prevent infections in wounds, while its anti-inflammatory effects can reduce redness and swelling. These combined properties make *Achillea millefolium* a potentially valuable natural remedy for skin healing, soothing irritated skin, and supporting overall skin regeneration.

An example of a yarrow extract in accordance with the present invention is commercially available from O&3, a company headquartered in Poland, in the form of an infusion in sunflower seed oil.

The yarrow extract is typically employed in the composition of the present disclosure in an amount of from about 0.01 to 4%, or from about 0.01 to about 2%, or from about 0.01 to about 1% by weight, all weights based on the total weight of the composition. In some embodiments, the yarrow extract is in the form of an infusion in sunflower seed oil.

In some embodiments, the composition of the present disclosure further contains at least one ingredient capable of emulsifying, stabilizing, and solubilizing the plant extracts of the present disclosure. An example of a suitable emulsifier for use in the invention is TWEEN®, a.k.a., Polysorbate. Tween is a compound created from sorbitol, a fatty acid, and ethylene oxide, which forms a nonionic surfactant used to emulsify and solubilize ingredients.

It should be noted, however, that any suitable emulsifier and/or solubilizer may be used without departing from the spirit of the invention, so long as it is vegan and dermatologically acceptable.

In some embodiments, the present disclosure provides a composition for treating damaged skin, the composition comprising: (a) from about 0.1 to about 5% by weight of *Padina pavonica* extract; (b) from about 0.1 to about 5% by weight of *Scutellaria baicalensis* extract; (c) from about 0.1 to about 5% by weight of *Physalis angulata* extract; and (d) from about 1 to about 5% by weight of an emulsifier, all weights based on the total weight of the composition. In some embodiments, the composition further comprises from about 0.01 to about 4% by weight of yarrow extract.

In some embodiments, the present disclosure further provides a composition for treating damaged skin, the composition comprising: (a) from about 0.5 to about 3% by weight of *Padina pavonica* extract; (b) from about 0.5 to about 3% by weight of *Scutellaria baicalensis* extract; (c) from about 0.5 to about 3% by weight of *Physalis angulata* extract; and (d) from about 1.5 to about 4% by weight of an emulsifier, all weights based on the total weight of the composition. In some embodiments, the composition further comprises from about 0.01 to about 2% by weight of yarrow extract.

In some embodiments, the present disclosure further provides a composition for treating damaged skin, the composition comprising: (a) from about 1 to about 2% by weight of *Padina pavonica* extract; (b) from about 1 to about 2% by weight of *Scutellaria baicalensis* extract; (c) from about 1 to about 2.5% by weight of *Physalis angulata* extract; and (d) from about 2 to about 3% by weight of an emulsifier, all weights based on the total weight of the composition. In some embodiments, the composition further comprises from about 0.01 to about 1% by weight of yarrow extract.

In some embodiments, the present disclosure further provides a composition for treating damaged skin, the composition comprising: (a) about 2% by weight of *Padina pavonica* extract; (b) about 2% by weight of *Scutellaria baicalensis* extract; (c) about 2.5% by weight of *Physalis angulata* extract; and (d) about 3% by weight of an emulsifier, all weights based on the total weight of the composition. In some embodiments, the composition further comprises from about 0.1 to about 1% by weight of yarrow extract.

The composition of the present disclosure may also include certain adjuvants that can further potentiate the optimization of skin healing and erythema reduction realized by the composition of the present disclosure. Examples of suitable adjuvants include groundcherry, milk thistle ester, and murumuru. In some embodiments, the adjuvant comprises a humectant.

In the event an adjuvant is employed, it may be used in an amount of from about 0.1 to about 5% by weight, or from about 0.5 to about 3% by weight, or from about 1 to about 2.5% by weight, or from about 1 to about 4% by weight, all weights based on the total weight of the composition.

The compositions of the present disclosure may be made available to consumers in a wide variety of product forms that include, but are not limited to, solutions, suspensions, lotions, creams, gels, sprays, ointment, foams, and serums.

According to embodiments of the present disclosure, the compositions can also additionally contain suitable optional ingredients as desired. For example, the composition can optionally include other active or inactive ingredients, provided they do not unacceptably alter the benefits of the skincare composition, are natural, and/or do not promote skin sensitization. The precise amount of optional ingredients will be determined by those skilled in the art.

In some embodiments, the composition is vegan, i.e., does not contain any animal products or animal byproducts.

In some embodiments, the pH of the composition is about 4.0 to about 6.0, or about 4.2 to about 5.8, or about 4.5 to about 5.5. In some embodiments, the pH of the composition is about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0.

In yet another embodiment of the present disclosure, there is provided a method of treating damaged skin comprising topically applying a composition comprising: (a) from about 0.1 to about 5% by weight of *Padina pavonica* extract; (b) from about 0.1 to about 5% by weight of *Scutellaria baicalensis* extract; (c) from about 0.1 to about 5% by weight of *Physalis angulata* extract; and (d) from about 1 to about 5% by weight of an emulsifier, all weights based on the total weight of the composition. In some embodiments, the composition further comprises from about 0.01 to about 4% by weight of yarrow extract.

According to yet another embodiment of the present disclosure, there is provided a method of treating damaged skin comprising topically applying composition comprising: (a) from about 0.5 to about 3% by weight of *Padina pavonica* extract; (b) from about 0.5 to about 3% by weight of *Scutellaria baicalensis* extract; (c) from about 0.5 to about 3% by weight of *Physalis angulata* extract; and (d) from about 1.5 to about 4% by weight of an emulsifier, all weights based on the total weight of the composition. In some embodiments, the composition further comprises from about 0.01 to about 2% by weight of yarrow extract.

Another embodiment of the present disclosure is directed to a method of treating damaged skin comprising topically applying a composition comprising: (a) from about 1 to about 2% by weight of *Padina pavonica* extract; (b) from about 1 to about 2% by weight of *Scutellaria baicalensis* extract; (c) from about 1 to about 2.5% by weight of *Physalis angulata* extract; and (d) from about 2 to about 3% by weight of an emulsifier, all weights based on the total weight of the composition. In some embodiments, the composition further comprises from about 0.01 to about 1% by weight of yarrow extract.

In further embodiments, the present disclosure provides a method of treating damaged skin comprising topically applying a composition comprising: (a) about 2% by weight of *Padina pavonica* extract; (b) about 2% by weight of *Scutellaria baicalensis* extract; (c) about 2.5% by weight of *Physalis angulata* extract; and (d) about 3% by weight of an emulsifier, all weights based on the total weight of the composition. In some embodiments, the composition further comprises from about 0.1 to about 1% by weight of yarrow extract.

In some embodiments, treatment of damaged skin comprises treating erythema and/or promoting skin healing. In some embodiments, the compositions and methods described herein treat erythema and promote skin healing.

EXAMPLES

The following examples as set forth herein are intended for illustrative purposes only and are not intended to limit the scope of the disclosure in any way, as many variations thereof are possible without departing from the spirit and scope of the disclosure. In the examples, all concentrations are listed as weight percent, unless otherwise specified.

Example 1

The following composition was prepared and tested in the following clinical studies:

TABLE 1

| Ingredient | % wt/wt |
|---|---|
| OCEA HEALTH ® (*Padina pavonica*) | 2 |
| SCUTALINE ® (*Scutellaria baicalensis*) | 2 |
| PHYSAVIE ® (*Physalis angulata*) | 2.5 |
| Emulsifier | 3 |
| Adjuvants | 3.8 |
| Auxiliaries | 17.1 |
| Water | q.s. 100 |

Clinical Study 1

The composition of Table 1 was clinically tested in order to determine its effect on UV-induced erythema. Twenty-one individuals (both male and female), aged 19-60 were irradiated with a xenon lamp simulator solar light multiport 601-300 Watt device.

Cutaneous hydration measurements were taken with a CORNEOMETER® CM 825 (Courage & Khazaka) at DO (prior to irradiation), DO 1-hour after irradiation, DO 5-hours after irradiation, and on D3 after irradiation.

The results showed that the composition of Table 1 yielded a significant increase in cutaneous hydration rate of approximately 14% on D3, which was observed in 90% of the test subjects, as compared to an un-treated zone.

Transepidermal water loss (TEWL) was also measured at DO (prior to irradiation), DO 1-hour after irradiation, DO 5-hours after irradiation, and on D3 after irradiation.

The results showed that the irradiated skin, treated with the composition of Table 1, experienced no significant change in TEWL on D3, indicating that cutaneous barrier state has been maintained post-treatment, as compared to the un-treated zone.

These clinical results establish the effectiveness of the composition of Table 1 in helping to repair and replenish the skin barrier, specifically with respect to its lipid matrix which enables moisture/hydration to be retained within the skin, by comparing the exposed treated zone versus the exposed untreated zone, whereby 90% of test subjects experienced a 14% increase in skin hydration after 3 days post-treatment, and the cutaneous skin barrier state being maintained, i.e., moisture remaining sealed within the skin barrier, as evidenced by no change in TEWL after 3 days post-treatment.

Next, the composition of Table 1 was clinically tested to assess its ability to effectively manage inflammation and oxidative stress after UV irradiation. Thirty-five individuals (both male and female), aged 21-57, were irradiated with a xenon lamp simulator solar light multiport 601-300 Watt device.

The degree of erythema experienced by study participants was assessed using a C-CUBE 2® (Pixience) dermoscope which optimally renders the full spectrum of the skin's natural colours, in order to arrive at an Erythema Index value. Erythema index is a specific C-CUBE parameter. Based on a* parameter, every pixel is used to grade erythema. It can be displayed with a blue/red color map to localize and illustrate the erythema.

Three zones on each participant's back were chosen and identified as (1) UV exposed and treated zone, (2) non-treated and UV exposed zone, and (3) non-treated and non-exposed zone. Participants were irradiated with UV light on DO with skin color measurements being taken with the C-Cube approximately 15 minutes after irradiation, after which the participants were sent home. On D1, approximately 24 hours later, the color of the test subjects' skin was again measured with the C-Cube, after which their skin was again irradiated with UV light but this time, the composition of Table 1 was applied onto the UV exposed and treated zone. On D2, approximately 24 hours later, the test subjects again returned to the test center to have their skin color measured.

The results showed that the composition of Table 1 resulted in a 34% decrease in erythemal index being experienced by 84% of the study participants, as compared to the untreated zone, corresponding to a marked decrease in erythema post-treatment.

Clinical Study 2

The composition of Table 1 was then evaluated to determine its effect on inflammation and oxidative stress post-irradiation with UV light. Skin samples were obtained from each participant using non-invasive cutaneous swabs. The collected swabs were then analyzed with respect to the following biomarkers: Squalene peroxide (SQOOH), Catalase (CAT), and SuperOxyde Dismutase (SOD).

UV rays generate free radicals in the skin and are a source of oxidative stress for the skin. Squalene monohydroperoxide (SQOOH) is a marker of reactive oxygen species (ROS)-mediated alterations caused by external UV exposure. Skin samples were collected with non-invasive cutaneous swabs, after which a measurement of squalene peroxide was taken using gas chromatography/mass spectrometry (GC/MS). The total protein concentration (in g/ml) was measured in parallel in the same samples. The final values of SQOOH were expressed in ng/mg proteins total.

The results showed that treatment of irradiated skin with the composition of Table 1 rendered an immediate curative effect by significantly reducing the UV exposure-stress effect on SQOOH with an antioxidant protective index of 18% on average.

Skin samples were also collected with non-invasive cutaneous swabs to assess catalase activity using a catalase fluorometric detection kit. The total protein concentration (in g/ml) was measured in parallel in the same samples. Oxidative stress causes reactive oxygen species (ROS) to be produced which, in turn, cause the level of hydrogen peroxide ($H_2O_2$) to increase, thereby stimulating catalase (CAT) production to break it down into water and oxygen, two compounds harmless to the cell. The greater the damage suffered by the skin, the more the level of catalase is impacted.

Here too, the data showed an immediate curative effect upon application of the composition of Table 1 which significantly reduced the UV exposure-stress effect on CAT with an antioxidant protective index of 71% on average.

Powerful antioxidants, SODs have the function of minimizing oxidative stress by trapping free radicals produced during cellular metabolism. They protect cell membranes, essential proteins, and DNA from damage. However, their levels naturally decline as we age leading to an accumulation of radical and oxidative damage.

UV rays can generate free radicals and are a source of oxidative stress for the skin. A higher level of detoxification enzymes is then needed triggering an increase in the amount of SOD to combat this type of aggression. However, when the concentration of free radicals is beyond the available SOD capacity, photo-oxidant damage is found.

Skin samples were collected with non-invasive cutaneous swabs to assess SOD activity using a color enzyme method. The total protein concentration (in g/ml) was measured in parallel in the same samples. The final values of SOD were expressed in UI/mg proteins total.

The results showed an immediate curative effect upon application of the composition of Table 1 by way of a significant reduction in UV exposure-stress effect on SOD with an antioxidant protective index of 58% on average.

The results of this study establish the ability of the composition of Table 1 to have an erythema repairing effect and strong antioxidant protective effect on skin damaged by UV light.

Summary of Post-UV Damage Clinical Results

The results of the two studies show that when it comes to effectively treating UV-damaged skin, the composition of Table 1 serves to: (1) repair/replenish the skin barrier by strengthening the barrier's lipid matrix, thereby enabling it to better retain moisture post-UV injury; and (2) promote skin healing by ameliorating inflammation and oxidative stress experienced by the skin to help facilitate the repair process by reducing erythema while increasing antioxidant protection for improved ROS scavenging and free radical quenching.

Example 2

A clinical study was conducted on a female test subject to assess the effectiveness of a composition in accordance with the present disclosure to assess its effectiveness in treating skin following a micro-needling procedure conducted in a dermatologist's office. FIG. 1 shows the unexpected results achieved by the composition. Viewing the photos from left to right, the first photo shows the side of the female test subject's face prior to micro-needling. The second photo was taken immediately after the micro-needling procedure, with the third and fourth photos evidencing the ability of the composition of the present disclosure to treat mechanically damaged skin in a synergistically-optimized fashion.

Example 3

Figure 2:
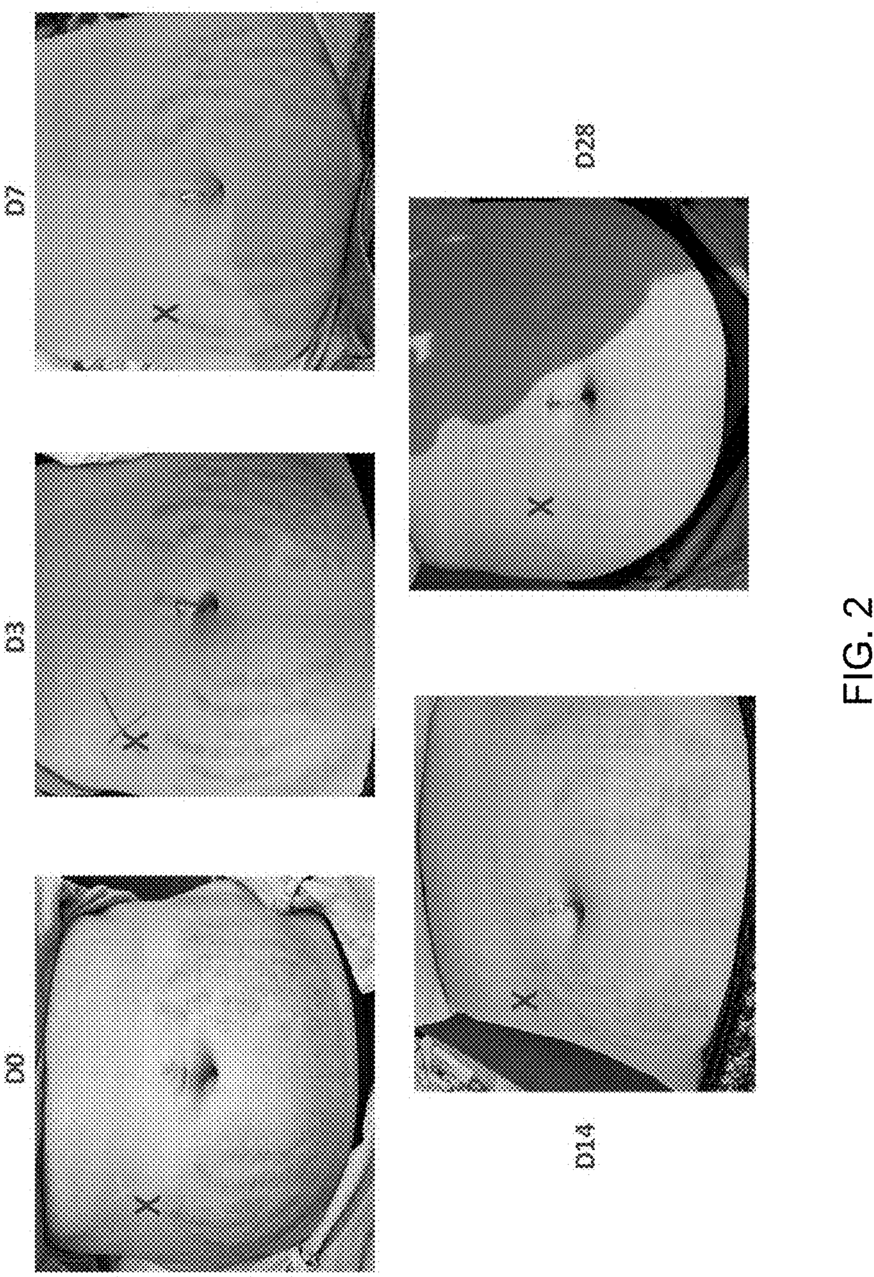
FIG. 2 is a series of frontal profile view photographs of a test subject's stomach following a laser CO2+IPL skin treatment procedure from D0 to D28, evidencing the ability of the composition of the present disclosure to effectively treat skin that has been damaged by mechanical stress, due to the synergistic skin healing properties exhibited by the composition of the present disclosure. The X-side of the stomach is where a composition in accordance with the present disclosure was applied, whereas the other side of the stomach is where a benchmark product was applied for comparison purposes.

A second clinical study was conducted on a test subject to assess the effectiveness of a composition in accordance with the present disclosure to assess its effectiveness in treating skin following a Intense Pulsed Light (IPL) and Fractional CO2 Laser ("IPL+$CO_2$) procedure. FIG. 2 shows the unexpected results achieved by the composition. The photos taken at DO, D3, D7, D14, and D28 show the progressive improvement in the affected skin, evidencing the ability of the composition of the present disclosure to treat laser damaged skin in a synergistically-optimized fashion.

Summary of Post-Mechanical Damage Clinical Results

The results of the two studies show that when it comes to effectively treating skin that has been damaged by mechanical stress (ex. micro-needling or laser ablation/hole drilling), the composition helps to facilitate healing in a synergistic fashion, as evidenced by FIGS. 1 and 2.

The skilled artisan will recognize the interchangeability of various components and ingredients from the embodiments described. Besides the variations described, other known equivalents for each feature can be mixed and matched by one of ordinary skill in the art to prepare a skincare composition under principles of the present disclosure. Therefore, the embodiments described may be adapted to compositions for any purpose and utilizing any suitable ingredient.

While the foregoing embodiments have been described, it is understood that alternatives and modifications of these embodiments, such as those suggested by others, may be made to fall within the scope of the disclosure.

What is claimed is:

1. A composition for treating damaged skin, the composition comprising: (a) from about 0.1 to about 5% by weight of *Padina pavonica* extract; (b) from about 0.1 to about 5% by weight of *Scutellaria baicalensis* extract; (c) from about 0.1 to about 5% by weight of *Physalis angulata* extract; (d) from about 0.01 to about 4% by weight of yarrow extract infused in sunflower seed oil; and (e) from about 1 to about 5% by weight of an emulsifier, all weights based on the total weight of the composition.

2. The composition of claim 1, wherein (a) is employed in an amount of from about 0.5 to about 3% by weight; (b) is employed in an amount of from about 0.5 to about 3% by weight; and (c) is employed in an amount of from about 0.5 to about 3% by weight, all weights based on the total weight of the composition.

3. The composition of claim 1, wherein (a) is employed in an amount of from about 1 to about 2% by weight; (b) is employed in an amount of from about 1 to about 2% by weight; and (c) is employed in an amount of from about 1 to about 2.5% by weight, all weights based on the total weight of the composition.

4. The composition of claim 1, wherein the damaged skin is caused by exposure to excess UV radiation.

5. The composition of claim 1, further comprising at least one adjuvant employed in an amount of from about 0.1 to about 5% by weight, based on the total weight of the composition.

6. The composition of claim 5, wherein the adjuvant is employed in an amount of from about 0.5 to about 3% by weight, based on the total weight of the composition.

7. The composition of claim 5, wherein the adjuvant is employed in an amount of from about 1 to about 2.5% by weight, based on the total weight of the composition.

8. The composition of claim 5, wherein the adjuvant comprises milk thistle ester, murumuru, a humectant, or mixtures thereof.

9. The composition of claim 1, wherein the damaged skin is caused by mechanical stress.

10. The composition of claim 1, wherein the yarrow extract infused in sunflower seed oil is employed in an amount of from about 0.01 to about 2% by weight, based on the total weight of the composition.

11. The composition of claim 1, wherein the yarrow extract infused in sunflower seed oil is employed in an amount of from about 0.01 to about 1% by weight, based on the total weight of the composition.

12. The composition of claim 1, wherein the composition is vegan and has a pH ranging from about 4.5 to about 5.5.

13. A method of treating damaged skin comprising topically applying a composition containing: (a) from about 0.1 to about 5% by weight of *Padina pavonica* extract; (b) from about 0.1 to about 5% by weight of *Scutellaria baicalensis* extract; (c) from about 0.1 to about 5% by weight of *Physalis angulata* extract; (d) from about 0.01 to about 4% by weight of yarrow extract infused in sunflower seed oil; and (e) from about 1 to about 5% by weight of an emulsifier, all weights based on the total weight of the composition.

14. The method of claim 13, wherein (a) is employed in an amount of from about 0.5 to about 3% by weight; (b) is employed in an amount of from about 0.5 to about 3% by weight; and (c) is employed in an amount of from about 0.5 to about 3% by weight, all weights based on the total weight of the composition.

15. The method of claim 13, wherein (a) is employed in an amount of from about 1 to about 2% by weight; (b) is employed in an amount of from about 1 to about 2% by weight; and (c) is employed in an amount of from about 1 to about 2.5% by weight, all weights based on the total weight of the composition.

16. The method of claim 13, wherein the damaged skin is caused by UV radiation.

17. The method of claim 13, further comprising at least one adjuvant employed in an amount of from about 0.1 to about 5% by weight, based on the total weight of the composition.

18. The method of claim 17, wherein the adjuvant is employed in an amount of from about 0.5 to about 3% by weight, based on the total weight of the composition.

19. The method of claim 17, wherein the adjuvant is employed in an amount of from about 1 to about 2.5% by weight, based on the total weight of the composition.

20. The method of claim 17, wherein the adjuvant comprises milk thistle ester, murumuru, a humectant, or mixtures thereof.

21. The method of claim 13, wherein the damaged skin is caused by mechanical stress.

22. The method of claim 13, wherein the yarrow extract infused in sunflower seed oil is employed in an amount of from about 0.01 to about 2% by weight, based on the total weight of the composition.

23. The method of claim 4, wherein the yarrow extract infused in sunflower seed oil is employed in an amount of from about 0.01 to about 1% by weight, based on the total weight of the composition.

24. The method of claim 13, wherein the composition is vegan and has a pH ranging from about 4.5 to about 5.5.

* * * * *